United States Patent [19]

Heyl et al.

[11] Patent Number: 5,165,918

[45] Date of Patent: Nov. 24, 1992

[54] ANTIMICROBIAL OPHTHALMIC SOLUTIONS CONTAINING DODECYL-DIMETHYL-(2 PHENOXYETHYL)-AMMONIUM BROMIDE AND METHODS OF USING THE SAME

[75] Inventors: Barbara L. Heyl, Atlanta; Lynn C. Winterton, Rosewell; Fu-Pao Tsao, Lawrenceville, all of Ga.

[73] Assignee: Ciba-Geigy Corporation, Ardsley, N.Y.

[21] Appl. No.: 461,366

[22] Filed: Jan. 5, 1990

Related U.S. Application Data

[63] Continuation of Ser. No. 212,486, Jun. 28, 1988, abandoned.

[51] Int. Cl.$^5$ .............................................. A61K 31/79
[52] U.S. Cl. .................................. 424/78.04; 252/106; 422/37; 514/643; 514/839; 514/912; 514/915
[58] Field of Search ............... 514/643, 839, 912, 915; 252/106; 424/78, 78.04; 422/37

[56] References Cited

U.S. PATENT DOCUMENTS

| | | | |
|---|---|---|---|
| 2,309,592 | 1/1943 | Hueter | 167/31 |
| 2,581,336 | 1/1952 | Hartmann et al. | 260/567.6 |
| 2,666,010 | 1/1954 | Stayner | 167/30 |
| 2,692,231 | 1/1955 | Stayner et al. | 210/23 |
| 2,904,468 | 9/1959 | Davis et al. | 167/58 |
| 2,977,280 | 3/1961 | Forsyth et al. | 167/53.2 |
| 3,279,981 | 10/1966 | Geiger et al. | 167/22 |
| 3,361,548 | 1/1968 | Smith et al. | 424/78 |
| 3,433,578 | 3/1969 | Reid | 21/53 |
| 3,549,747 | 12/1970 | Krezanoski et al. | 424/78 |
| 3,639,576 | 2/1972 | Kaspar et al. | 424/78 |
| 3,882,036 | 3/1975 | Krezanoski et al. | 424/78 |
| 4,013,576 | 3/1977 | Loshaek | 252/106 |
| 4,029,817 | 6/1977 | Blanco et al. | 424/329 |
| 4,039,662 | 8/1977 | Hecht et al. | 424/180 |
| 4,407,791 | 10/1983 | Stark | 424/80 |
| 4,525,346 | 7/1985 | Stark | 424/80 |
| 4,529,535 | 7/1985 | Sherman | 252/106 |
| 4,532,128 | 7/1985 | Sheldon et al. | 424/78 |
| 4,615,882 | 10/1986 | Stockel | 424/78 |

FOREIGN PATENT DOCUMENTS

| | | | |
|---|---|---|---|
| 607222 | 8/1948 | United Kingdom | 514/643 |
| 1292412 | 10/1972 | United Kingdom | 424/78 |

OTHER PUBLICATIONS

Easterbrook et al., Canad. J. Ophthal., vol. 4 (1969), pp. 247–256.

*Primary Examiner*—Lester L. Lee
*Attorney, Agent, or Firm*—Wenderoth, Lind & Ponack

[57] ABSTRACT

The invention relates to the use of dodecyl-dimethyl-(2 phenoxyethyl)-ammonium bromide as an antimicrobial agent to be a preservative for ophthalmic drug solutions, in disinfecting solutions, as well as in preservatives for aqueous ocular solutions for contact lenses.

10 Claims, No Drawings

ANTIMICROBIAL OPHTHALMIC SOLUTIONS CONTAINING DODECYL-DIMETHYL-(2 PHENOXYETHYL)-AMMONIUM BROMIDE AND METHODS OF USING THE SAME

CROSS-REFERENCE TO RELATED APPLICATION

This application is a continuation application of Ser. No. 07/212,486 filed Jun. 28, 1988, now abandoned.

BACKGROUND OF THE INVENTION

The present invention relates to ophthalmic solutions utilizing dodecyl-dimethyl-(2 phenoxyethyl)-ammonium bromide. The eye, and particularly the conjunctiva, offers an ideal environment for many types of organisms. Infections of the eye can be very serious. For example, Pseudomonas aeruginosa is a particularly dangerous and opportunistic organism, and has been known to cause infections which progress so rapidly that loss of the eye can occur in as short a period as twenty-four hours after onset. For this reason, it is important that solutions used in connection with the eye, such as preserved ophthalmic solutions and contact lens disinfecting solutions, be as effective antimicrobial agents as possible.

Presently, there is not a problem-free preservative available for ophthalmic use. Preservatives presently in use in ophthalmic solutions include benzalkonium chloride, chlorhexidine, Thimerosal and chlorobutanol. However, at the concentrations needed to be effective, these compounds have high ocular toxicity or sensitivity. For example, if used repeatedly in concentrations of 1:5,000 or stronger, benzalkonium chloride can denature the corneal protein causing irreversible damage. Other known preservatives, such as Onamer M and sorbic acid, are not very effective and therefore have short product shelf lives.

There exists, therefore, a need for improved ophthalmic solutions which are both effective as antimicrobial agents and which are also ocularly compatible.

There are several patents which disclose the use of quarternary ammonium compounds in contact lens solutions, including the following, but all of the disclosed compositions have certain disadvantages:

| U.S. Pat. No. | Inventor |
|---|---|
| 3,549,747 | Krezanoski et al. |
| 3,639,576 | Kaspar et al. |
| 4,013,576 | Loshaek |
| 4,029,817 | Blanco et al. |
| 4,039,662 | Hecht et al. |
| 4,361,548 | Smith et al. |

There also exists a need for improved ophthalmic solutions which have a longer shelf life.

SUMMARY OF THE INVENTION

In accordance with this invention, there is provided ophthalmic solutions having as the active antimicrobial agent dodecyl-dimethyl-(2 phenoxyethyl)-ammonium bromide. The compound has been found to be effective, for example, as a preservative in saline at concentrations as low as 5 ppm, and as a disinfectant at concentrations as low as 30 ppm.

It has also been found that the presence of ethylenediaminetetraacetic acid, or EDTA, in addition to the dodecyl-dimethyl-(2 phenoxyethyl)-ammonium bromide, leads to increased antimicrobial action far exceeding that previously noted for quaternary ammonium compounds.

Typically, a solution utilizing the present invention may be a preserving and/or disinfecting solution for contact lenses, or an ophthalmic drug. Such solutions prepared according to the present invention have been found to be both effective as antimicrobial agents, as well as ocularly compatible.

DESCRIPTION OF THE PREFERRED EMBODIMENTS

Dodecyl-dimethyl-(2 phenoxyethyl)-ammonium bromide has the general formula:

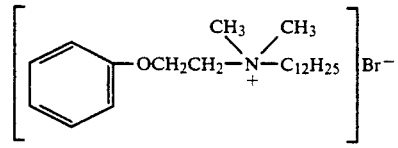

and is available commercially as "Bradosol ®", a trademark of Ciba Geigy Corporation. Bradosol ® belongs to a family of compounds known as quaternary ammonium salts, and has high bactericidal, bacteriostatic and fungicidal activity, even at very low concentrations. It has been used previously in medical applications including surgical scrubs, instrument storage and throat lozenges.

It has now been found that dodecyl-dimethyl-(2 phenoxyethyl)-ammonium bromide is significantly less irritating than other antimicrobial agents, and particularly other quarternary compounds used in ophthalmic solutions. For purposes herein, an ophthalmic solution is defined as a solution used in connection with the eye. It has also been found that, in combination with ethylenediaminetetraacetic acid, or EDTA, its antimicrobial properties are greatly enhanced. As such, dodecyl-dimethyl-(2 phenoxyethyl)-ammonium bromide can be effectively used as a preservative for ophthalmic drug solutions, or in disinfecting solutions, as well as in preservatives for aqueous ocular solutions for contact lenses.

It has also been found that solution component interaction is important to the effectiveness of dodecyl-dimethyl-(2 phenoxyethyl)-ammonium bromide in solutions such as suggested here. For example, Bradosol ® is compatible with lactate, tartrate, phosphate, borate, carbonate, and citrate buffer systems to provide the proper pH for use in the eye. The solution is typically maintained at an osmotic pressure similar to that of physiological saline (0.9% saline). However, the presence of polymers such as polyvinyl alcohol cause a decrease in effectiveness, so higher concentrations of the Bradosol ® are needed to preserve such a solution. The same is true for surfactants such as those used in contact lens cleaning solutions. It is believed that this is a result of the interaction of the quaternary nitrogen (+ charged) with various groups, thereby leaving less dodecyl-dimethyl-(2 phenoxyethyl)-ammonium bromide free in solution. Because the nitrogen is positively charged, components with a strong negative charge bind the Bradosol ® completely. As such, negatively charged compounds or drugs are not effectively preserved by the present invention.

Examples of ophthalmic drugs which can use Bradosol ® as a preservative, typically at a range between 0.001% to 1%, include:

| DRUG | USE |
| --- | --- |
| Proparacaine.HCl | Anesthetic |
| Tetracaine.HCl | Anesthetic |
| Carbachol | Glaucoma |
| Pilocarpine | Glaucoma |
| Physostigmine.SO$_4$ | Glaucoma |
| Homatropine | Mydriatic |
| Idoxuridine | Herpes |
| Dexamethasone | Inflammation |
| Prednisolone | Inflammation |
| Epinephrine.HCl | Glaucoma |
| Epinephrine.borate | Glaucoma |
| Phenylephrine.HCl | Decongestant |
| Atropine sulfate | Mydriasis |
| Cyclopentolate.HCl | Mydriasis |

The following examples of other ophthalmic solutions using dodecyl-dimethyl-(2 phenoxyethyl)-ammonium bromide are illustrative only and should not be construed as limiting the invention.

EXAMPLE I

Preserved Cleaner For Contact Lenses

| | |
| --- | --- |
| Na$_2$HPO$_4$ | 0.7287% (wt/vol) |
| NaH$_2$PO$_4$.H$_2$O | 0.2116% (wt/vol) |
| Na$_2$(EDTA).2H$_2$O | 0.1000% (wt/vol) |
| Bradosol ® (dodecyl-dimethyl-(2 phenoxyethyl)-ammonium bromide | 0.0080% (wt/vol) |
| NaCl | 0.3552% (wt/vol) |
| Varox ® 365 | 1.0000% (vol/vol) |
| Triton ® X-100 | 0.3333% (vol/vol) |
| Cellosize ® QP-40 HEC | 1.5000% (wt/vol) |
| Purified H$_2$O | q.s. 100 ml |

The preserved cleaner set forth in Example I, which utilizes a preferred minimum of approximately 80 ppm Bradosol ®, has a pH of 7.20±0.1 and has an osmolarity of 300±10 mOsm/kg. Although the formulation contains Bradosol ®, it was found to be effective and compatible with all types of contact lenses, including those containing HEMA. It is believed that the short contact time for cleaning and the disinfection step which follows for HEMA lenses results in less absorption into the lens.

A phosphate buffer system is set forth, although a borate, citrate, acetate or Tris buffer system, or combinations thereof, could be used with equal efficacy. The concentration of the buffer can be easily modified and specified by those familiar with buffering systems. The system should be such as to keep the Bradosol ® within a range of 6.5-8.0, with the preferred range being near to pH 7.0-7.4, where it is most effective.

EDTA is used for two purposes. First, it acts as a chelating agent for ions that typically adhere to contact lenses and form undesired deposits. Second, it was found that EDTA, in combination with Bradosol ®, and particularly at approximately 0.1% (wt/vol.) has a synergistic effect and gives a greater increase in effectiveness to the Bradosol ® than previously noted for quarternary ammonium compounds. For example, the following table summarizes preservative effectiveness tests utilizing the cleaner of Example I:

| Microorganism | Number of Surviving Microorganisms (CFU ml) | | | | | | | |
| --- | --- | --- | --- | --- | --- | --- | --- | --- |
| | Initial (0) | 6h | 24h | 48h | 7d | 14d | 21d | 28d |
| Aspergillus niger | 10$^6$ | — | — | — | 10$^3$ | 10$^2$ | 10$^2$ | 10$^2$ |
| Candida albicans | 10$^6$ | — | — | — | 0 | 0 | 0 | 0 |
| Pseudomonas aeruginosa | 10$^6$ | 0 | 0 | 0 | 0 | 0 | 0 | 0 |
| Staphylococcus aureus | 10$^6$ | 0 | 0 | 0 | 0 | 0 | 0 | 0 |

The EDTA level can be modified up to a maximum of 0.2% (by weight) and as low as 0%.

Sodium chloride is used to adjust the osmolarity of the solution to a desired level. Other inorganic and organic salts may be used, but sodium chloride is preferred for ease of obtaining a pure, reproducible salt. The osmolarity of the solution of Example I can be adjusted to 300±50 without any apparent disadvantage.

Varox ® 365, a trademark of Sherex Chemical, is an amine oxide surfactant used for solubilizing grease and dirt that typically do not naturally occur in vivo, such as cosmetics and body oils. While the 1.0000% set forth in Example I is considered optimal, the amount of amine oxide surfactant used may range from 0.3% to 3.0%. Furthermore, Varox ® 365 is a good foaming agent, which is desirable in a cleaning solution. The Varox ® 365 can be replaced by other "true" nonionic surfactants and those amine oxides that exhibit little or no affinity to the dodecyl-dimethyl-(2 phenoxyethyl)-ammonium bromide.

The Triton ® X-100, a trademark of Rohm and Haas, is primarily used as a surfactant for proteins, lipids, dirt, and other debris that occur in vivo with contact lens wear. Most of the Triton series could be used, yet Triton ® X-100 is preferred. Although it is widely held that Triton ® is potentially dangerous for use in the eye, the percentage used in the solution of Example I has shown no more than transient reddening of the eye that clears within one hour. It has been found that an increase in the amount of detergent in the solution requires an increase in the amount of Bradosol ® used.

Cellosize ® QP-40, a trademark of Union Carbide, is a quick dissolving hydroxyethyl cellulose used to adjust the viscosity of the solution to a desired level. However, any of the cellulosic derivatives could be used, as may be other viscosity builders such as the Carbopols, to provide the preferred viscosity of from 3 to 25 cps (Brookfield Spindle).

EXAMPLE II

Conditioning Solution for Gas Permeable and Hard Contact Lenses

| | |
| --- | --- |
| Na$_2$HPO$_4$ | 0.7193% (wt/vol) |
| NaH$_2$PO$_4$.H$_2$O | 0.2208% (wt/vol) |
| Na$_2$(EDTA).2H$_2$O | 0.1% (wt/vol) |
| Bradosol ® (dodecyl-dimethyl-(2 phenoxyethyl)-ammonium bromide | at least 0.0050% (wt/vol) (a range of 0.0035%-1.0%) |
| NaCl | 0.4383% (wt/vol) |
| Vinol ® 350 PVA | 0.5% (wt/vol) |
| Plasdone K-90 PVP | 1.0% (wt/vol) |
| Purified H$_2$O | q.s. 100 ml |

The solution for disinfecting and soaking gas permeable contact lenses set forth in Example II has a pH of 7.40±0.1 and an osmolarity of 300±100 mOsm/kg.

The particular solution used in Example II contains approximately 0.0035% to 1.0% (wt/vol) Bradosol ®, and preferably 0.0050% (wt/vol). The wetting exhibited by this solution is superior to all known conditioners, and is retained for longer than would be expected from such a solution.

The phosphate buffering system is important to the solution of Example II, since the PVA is incompatible with borate, citrate, and acetate buffering systems. However, any PVA compatible buffer may be used.

The EDTA and sodium chloride are used in a similar fashion as set forth in detail in the description of Example I, above.

Vinol ® 350 PVA is a trademark of Air Products, Inc. It is preferred in the disinfecting and soaking solution to use specified grades of PVA. PVA exhibits better wetting as its molecular weight increases and as its degree of hydrolysis decreases. However, these characteristics present manufacturing problems in that increased molecular weight results in slower solubilization and more viscous solutions, while as the degree of hydrolysis decreases, the solubilization of PVA decreases. It has been found that, for best results in a solution such as Example II, a 70% hydrolyzed product should be used. The concentration of PVA is effective at amounts as high as 3% by weight and as low as 0.25% by weight. As the concentration of PVA drops below 1.0% by weight, the concentration of Plasdone K-90 PVP must be increased to offset the losses of wettability.

Plasdone K-90 PVP, a product of GAF, or povidone, has been found to have a synergistic wetting effect when used in combination with Vinol ® 350 PVA. While Plasdone K-30 may be used, it is not as effective as the K-90. The concentration of PVP depends upon the concentration of PVA utilized as noted above. At amounts above 0.75% by weight PVA, there is no discernable advantage by using more than equivalent percentages of PVP, although at this level one should not use less than the PVA concentration. Below 0.75% by weight, various properties were shown with differing PVA/PVP concentrations. PVP and PVA have been used in concentrations of from 0.25% to 3.0% by weight.

The following Table II presents a summary of preservative effectiveness tests utilizing the formulation of Example II:

| Microorganism | Number of Surviving Microorganisms (CFU ml) | | | | | | |
|---|---|---|---|---|---|---|---|
| | Initial (0) | 6h | 24h | 48h | 7d | 14d | 21d | 28d |
| Aspergillus niger | $10^6$ | — | — | — | $10^4$ | $10^2$ | $10^2$ | $10^2$ |
| Candida albicans | $10^6$ | — | — | — | 0 | $10^2$ | 0 | 0 |
| Pseudomonas aeruginosa | $10^6$ | 0 | 0 | 0 | 0 | $10^2$ | 0 | 0 |
| Staphylococcus aureus | $10^6$ | 0 | 0 | 0 | 0 | 0 | 0 | 0 |

It must be noted that the disinfecting and soaking solution set forth in Example II is not recommended for use with HEMA lenses. The Bradosol ® is present at such concentrations as to be taken up and concentrated into the matrix of these lenses upon extended contact time; i.e., greater than 30 minutes. Such concentrations of Bradosol ® may result in cytotoxicity.

EXAMPLE III

Neutralizing Conditioner for Hard Contact Lenses

| | |
|---|---|
| $Na_2HPO_4$ | 0.7193% (wt/vol) |
| $NaH_2PO_4.H_2O$ | 0.2208% (wt/vol) |
| $Na_2(EDTA).2H_2O$ | 0.1% (wt/vol) |
| Bradosol ® (dodecyl-dimethyl-(2 phenoxyethyl)-ammonium bromide | 0.0015% (wt/vol) |
| NaCl | 0.3214% (wt/vol) |
| Vinol ® 165 (or Vinol ® 350) | 1.0% (wt/vol) |
| Plasdone K-90 PVP | 1.0% (wt/vol) |
| Catalase | 700 units/ml |
| $H_2O$ | q.s. 100 ml |

The conditioner set forth in Example III has a pH of 7.20±0.1 and has an osmolarity of 300±10 mOsm/Kg. The amount of Bradosol ® used ranges from approximately 0.0015% (wt/vol) to approximately 1% (wt/vol.). It has been found that the catalase enhances the effectiveness of the Bradosol ®. In preparation, the $Na_2HPO_4$, $NaH_2PO_4.H_2O$, $Na_2(EDTA).2H_2O$, Bradosol ®, and NaCl should be added separately and stirred until dissolution is complete. The temperature of the broth should remain at ambient during the process. The Vinol ® 165 (or Vinol ® 350) is then added and the solution is stirred vigorously. The Plasdone K-90 should be added once the Vinol ® has formed a suspension with the solution. After the addition of the Plasdone K-90, the solution should be heated to 85–86° C. Dissolution of these items will take from about 30 to 50 minutes. For sterilization, the solution can be autoclaved at 121° C. for 30 minutes. The catalase should be micro filtered (0.2 m) into the main reactor only after the solution has reached 20–21° C.

The following Table III presents a summary of preservative effectiveness tests utilizing the formulation of Example III:

| Microorganism | Number of Surviving Microorganisms (CFU ml) | | | | | | |
|---|---|---|---|---|---|---|---|
| | Initial (0) | 6h | 24h | 48h | 7d | 14d | 28d |
| Aspergillus niger | $6.5 \times 10^4$ | — | — | — | $3.9 \times 10^2$ | $2.9 \times 10^2$ | $2.4 \times 10^2$ |
| Candida albicans | $8.3 \times 10^5$ | — | — | — | 0 | 0 | 0 |
| Pseudomonas aeruginosa | $2.7 \times 10^6$ | 0 | 0 | 0 | 0 | 0 | 0 |
| Staphylococcus aureus | $3.0 \times 10^6$ | 0 | 0 | 0 | 0 | 0 | 0 |

SUMMARY OF RANGES OF EFFECTIVENESS

In the presence of EDTA, dodecyl-dimethyl-(2 phenoxyethyl)-ammonium bromide has been found to be effective as a preservative in saline as low as 10 ppm. When there is interaction of the Bradosol ® with other components of a solution, as in the examples provided, a higher concentration is preferred. In the cleaner of Example I, the level was found to be 80 ppm. In the conditioner of Example III, the level was 15 ppm. When relatively small changes in the formulation are made, the Bradosol ® must be adjusted to ensure a preserved solution. Examples of solutions which have been tested and results of BP testing are shown in Table IV:

TABLE IV

| Solution | Bradosol ® | Pass/Fail |
|---|---|---|
| saline + EDTA | 10 ppm | P |
| saline + EDTA | 20 ppm | P |
| saline + EDTA | 50 ppm | PP |
| saline + EDTA | 75 ppm | PP |
| saline | 40 ppm | P |
| conditioner (PVA + PVP) + catalase | 15 ppm | P |
| conditioner + catalase | 30 ppm | P |
| conditioner/no catalase | 15 | F |
| conditioner/no catalase | 30 | P |
| conditioner/no catalase | 50 | P |
| cleaner (anionic detergent) | 100 ppm | F |
| cleaner (all nonionic) | 80 | P |

(Note:
Table IV is based upon the following:
BP TESTING
Use organisms:
*Aspergillus niger*
*Candida albicans*
*Pseudomonas aeruginosa*
*Staphyloccus aureus*
Requirements state: A three log reduction or greater in bacteria per ml within 6 hr, no bacteria at 24 hr or after. Fungi reduced by 2 logs within 7 days, no increase after.)

It has also been found that only a slightly higher concentration of Bradosol ® is required for disinfection than for a preservative; the distinction being the ability not just to prevent growth of organisms in the solution, but to kill ones actually introduced. It was found that a conditioner formula could obtain rapid kill times (especially with bacteria) using concentrations of 50 ppm Bradosol ®, as summarized in Table V, below. This is important since most conditioning type solutions are not disinfecting as well.

TABLE V

Conditioner With Bradosol ® Kill Times.

| | Time (min.) | | | | |
|---|---|---|---|---|---|
| | 0 | 1 | 3 | 5 | 15 |
| *S. aureus* Bradosol ® | | | | | |
| .0015% | $10^6$ | $10^6$ | $10^4$ | $10^4$ | $10^2$ |
| .003% | $10^6$ | $10^6$ | $10^4$ | $10^2$ | $10^1$ |
| .005% | $10^6$ | $10^5$ | $10^3$ | $10^2$ | $10^1$ |
| .01% | $10^6$ | $10^2$ | $10^1$ | $10^1$ | $10^1$ |
| *A. niger* at 3 hr. Bradosol ® | | | | | |
| .0015% | $10^5$ | | | | |
| .003% | $10^4$ | | | | |
| .005% | $10^2$ | | | | |
| .01% | $10^2$ | | | | |

In saline, disinfection was achieved at concentrations as low as 30 ppm, as summarized in Table VI below.

TABLE VI

Kill Times For Bradosol ® Containing Saline

| Time (min.) | .003% | .005% | .007% |
|---|---|---|---|
| *P. aeruginosa* | | | |
| 0 | $10^6$ | $10^6$ | $10^6$ |
| 5 | 0 | 0 | 0 |
| 10 | 0 | 0 | 0 |
| 15 | 0 | 0 | 0 |
| *S. aureus* | | | |
| 0 | $10^6$ | $10^6$ | $10^6$ |
| 5 | $10^3$ | $10^2$ | 0 |
| 10 | $10^1$ | 0 | 0 |

TABLE VI-continued

Kill Times For Bradosol ® Containing Saline

| Time (min.) | .003% | .005% | .007% |
|---|---|---|---|
| 30 | 0 | 0 | 0 |

It has also been determined that dodecyl-dimethyl-(2 phenoxyethyl)-ammonium bromide has relatively low ocular toxicity. Rabbit testing was performed using standard Draize testing. Using benzalkonium chloride at 40 ppm as a control, Bradosol ® was administered to eyes at concentrations of 100, 500, and 1000 ppm. No reaction was seen at 1000 ppm. Benzalkonium chloride, when administered ocularly at 1000 ppm, caused severe reaction and could only be administered once. Using Bradosol ®, no reaction was seen after administration over 21 days at 100 ppm.

While the above description contains many specificities, these should not be construed as limitations on the scope of the invention, but rather as exemplifications of certain preferred embodiments thereof. It will be understood that variations and modifications can be effected within the spirit and scope of the invention as previously described and as defined by the claims.

What is claimed is:

1. An ophthalmic solution comprising 0.0005 to 0.01 weight percent dodecyl-dimethyl-(2 phenoxyethyl)-ammonium bromide as an antimicrobial agent and approximately 0.1 weight percent of EDTA.

2. The ophthalmic solution of claim 1, wherein said solution further comprises an effective amount of buffer to provide said solution with an ophthalmically acceptable pH.

3. The ophthalmic solution of claim 1, wherein said solution is a preserved saline solution.

4. The ophthalmic solution of claim 1, wherein said solution is a disinfecting solution and wherein said dodecyl-dimethyl-(2 phenoxyethyl)-ammonium bromide is present in an amount of at least 0.0030 weight percent of said solution.

5. The ophthalmic solution of claim 1, wherein said solution is a conditioner for contact lenses and wherein said dodecyl-dimethyl-(2 phenoxyethyl)-ammonium bromide is present in an amount from approximately 0.0035 to approximately 0.01 weight percent of said solution.

6. The ophthalmic solution of claim 5, wherein said dodecyl-dimethyl-(2 phenoxyethyl)-ammonium bromide is present in an amount of approximately 0.0050 weight percent of said solution.

7. The ophthalmic solution of claim 1, wherein said solution is a neutralizing conditioner for contact lenses and said dodecyl-dimethyl-(2 phenoxyethyl)-ammonium bromide is present in an amount from approximately 0.0015 to approximately 0.01 weight percent of said solution, and wherein said solution further comprises effective amounts of catalase.

8. The ophthalmic solution of claim 7, wherein said catalase is present in an amount of at least approximately 0.03 weight percent of said solution.

9. The ophthalmic solution of claim 1, wherein said solution is a cleaner for contact lenses, and wherein said dodecyl-dimethyl-(2 phenoxyethyl)-ammonium bromide is present in an amount of at least approximately 0.0080 weight percent of said solution.

10. The ophthalmic solution of claim 1, wherein said solution is an ophthalmic drug solution, and wherein said dodecyl-dimethyl-(2 phenoxyethyl)-ammonium bromide is present in an amount from approximately 0.001% to 0.01%.

* * * * *